United States Patent [19]

Shiratori et al.

[11] 4,407,778

[45] Oct. 4, 1983

[54] FREON GAS DETECTING ELEMENT

[75] Inventors: Masayuki Shiratori, Kawasaki; Masaki Katsura, Yososuka, both of Japan

[73] Assignee: Tokyo Shibaura Denki Kabushiki Kaisha, Kawasaki, Japan

[21] Appl. No.: 293,963

[22] Filed: Aug. 18, 1981

[30] Foreign Application Priority Data

Sep. 25, 1980 [JP] Japan .................................. 55-132353
Sep. 25, 1980 [JP] Japan .................................. 55-132354
Sep. 25, 1980 [JP] Japan .................................. 55-132355

[51] Int. Cl.³ .............................................. G01N 27/12
[52] U.S. Cl. .................................. 422/90; 324/71.5; 338/225; 422/98; 436/126
[58] Field of Search ............... 338/225 D, 34; 422/90, 422/94-98, 93; 324/71 SN; 436/126

[56] References Cited

U.S. PATENT DOCUMENTS 4,045,178  8/1977  Okinaka et al. ...................... 422/98
4,259,292  3/1981  Ichinose et al. ..................... 422/98

Primary Examiner—Michael S. Marcus
Attorney, Agent, or Firm—Cushman, Darby & Cushman

[57] ABSTRACT

Freon gas detecting element for detecting the presence of freon gas with of a pair of electrodes, a gas detecting body made of a metal oxide semiconductor and covering the pair of electrodes, and a catalytic layer coated on the gas detecting body. The catalyst layer is made of at least one element selected from the group consisting of V, Mo and W supported by one catalyst carrier selected from the group consisting of $Al_2O_3$, $SiO_2$, and $SiO_2$-$Al_2O_3$.

6 Claims, 2 Drawing Figures

FREON GAS DETECTING ELEMENT

BACKGROUND OF THE INVENTION

This invention relates to a freon gas detecting element for detecting the presence of freon gas.

Freon gas is used as coolant for cooling apparatus such as electric refrigerators, air conditioners and the like. Leak of the freon gas from the cooling apparatus worsens cooling ability. Therefore leak of the freon gas has to be detected by a device having high stability and high detecting sensitivity.

There are known two types of freon gas leak detectors as described, for example, in a paper entitled "Halogen Leak Test" by Takeo Tsuchiya, *Journal of the Vacuum Society of Japan*, Vol. 22. No. 2, 1979. One is a cation emission type leak detector, and the other is a electric discharge halogenated hydrocarbon gases type leak detector. The cation emission type leak detector comprises a cylindrical ion collector (cathode) made of Pt, and an anode inside the cylindrical ion collector which is made of ceramics including substantial amounts of an alkali element such as Na or K. The anode is provided with a filament made of Pt wound around the outer periphery thereof and heated to about 800° C. by passing current through the filament. When the freon gas comes between the anode and the ion collector, the high temperature alkali, such as Na or K, on the surface of the ceramics exchanges electrons with the haloid compound which has strong electron affinity. As the result, cations of $Na^+$ and $K^+$ are produced and flow into the ion collector. The leaking freon gas, thereby, can be detected.

However, it is difficult for the freon gas detector of this type to be miniaturized because it must be provided with a heating mechanism for heating the ceramics to high temperature (800° C.). Also, the stability and detecting sensitivity are inadequate. Particularly, a large quantity of $Na^+$ or $K^+$ is released from the surface of the ceramics when substantial amounts of freon gas are leaking. As a result, the detecting sensitivity is low until the element recovers. Further, the reliability of the detector is not sufficient because the detector is also sensitive to other gas besides freon gas.

On the other hand, the electric discharge halogenated hydrocarbon gases type leak detector is provided with a pair of needle electrodes facing each other with a gap therebetween. To the electrodes is applied a high voltage (0.8–2 K) for producing a silent discharge at the gap. When the freon gas comes into the gap, the discharge is interrupted. As a result, the freon gas is detected.

Further, in a detector of this type, high voltage has to be applied and the amount of freon gas can not be measured quantitatively. In addition, the discharge may be interrupted by other causes besides freon gas, for example, wind. Therefore the reliability of the detector is not sufficient.

SUMMARY OF THE INVENTION

It is an object of this invention to provide a small sized freon gas detecting element which has excellent stability of detecting sensitivity and high reliability. It is another object of this invention to provide a freon gas detecting element which has excellent detecting sensitivity for freon gas in low concentrations as well as high concentrations.

The freon gas detecting element of this invention comprises a pair of electrodes, a gas detecting body made of metal oxide semiconductor spread on the pair of electrodes, and a catalyst layer coated on the gas detecting body, the catalyst layer being made of at least one element selected from the group consisting of vanadium (V), molybdenum (Mo), and tungsten (W) supported by one catalyst carrier selected from the group consisting of $Al_2O_3$, $SiO_2$, and $SiO_2\text{-}Al_2O_3$.

BRIEF DESCRIPTION OF THE DRAWINGS

Other objects and features of the invention will become apparent to those skilled in the art as the disclosure is made in the following description of a preferred embodiment of the invention, as illustrated in the accompanying drawings, in which.

DETAILED DESCRIPTION OF THE INVENTION

The freon gas detecting element according to this invention includes a metal oxide semiconductor. The metal oxide semiconductor exhibits the characteristic that its surface resistance is varied in response to contact with the freon gas. For example, when an N-type semiconductor made of ZnO, $SnO_2$, $Fe_2O_3$ or the like comes into contact with freon gas, its surface resistance is lowered. Conversely, when the P-type metal oxide semiconductor comes into contact with freon gas, its surface resistance is elevated. Therefore, the presence of the freon gas may be detected by detecting the variation of the surface resistance of the metal oxide semiconductor.

Figure 1:
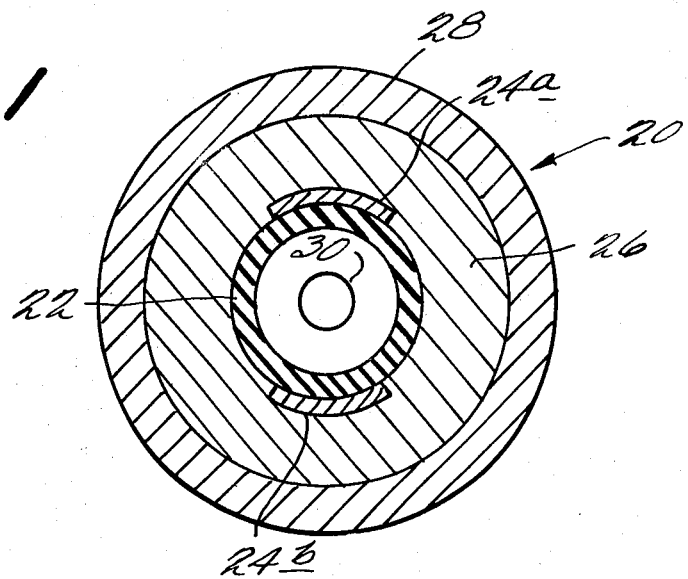
FIG. 1 is a cross-sectional view of a freon gas detecting element according to the present invention.

Now referring to FIG. 1, there is illustrated one embodiment of a freon gas detecting element according to this invention. The freon gas detecting element 20 comprises a hollow cylindrical insulative body 22, a pair of electrodes 24a and 24b provided on the outer periphery of insulative body 22, a gas detecting body 26 made of metal oxide semiconductive material and covering insulative body 22 and electrodes 24a and 24b. Further, a catalyst layer 28 about 10 to 100 microns thick is coated on the outer periphery of gas detecting body 26. In the hollow interior of insulative body 22 is disposed a heater 30 to heat gas detecting body 26. Heater 30, which is employed to elevate the gas sensitivity of gas detecting body 26, may be a coil type or any other type. It may be detachably disposed in hollow cylindrical insulative body 22, and thus may be taken out from the interior of insulating body 22 when unnecessary.

Hollow cylindrical insulating body 22 may be made of any electrically insulative material that remains heat-resistant at the temperature at which gas detecting element 20 is used. For example, it may be made of ceramics such as $SiO_2\text{-}Al_2O_3$ and $Al_2O_3$.

Gas detecting body 26 may be made of any metal oxide semiconductor where surface resistance varies when it comes into contact with freon gas. For example, it may be made of ZnO, $SnO_2$, $Fe_2O_3$, $ZnO\text{-}Me_2O_3$ (Me=Sb or Cr), $SnO_2\text{-}Me_2O_3$ (Me=Sb or Cr), $Fe_2O_3\text{-}Me_2O_3$ (Me=Sb or Cr). The gas selectivity, i.e., reactivity with freon gas, of such a metal oxide semiconductor is determined by its surface temperature, surface electron level, porosity, pore size, etc. Generally, however, such a metal oxide semiconductor body alone cannot make a satisfactory gas detecting element since its gas sensitivity and gas selectivity are insufficient.

Catalyst layer 28, therefore, is coated on the outer periphery of the gas detecting body to elevate the gas sensitivity and the gas selectivity of gas detecting body 26. The material of catalyst layer 28 must be selected carefully to obtain excellent gas sensitivity and selectivity. The catalyst layer 28 according to this invention is made of at least one element selected from the group consisting of V, Mo, and W supported by one catalyst carrier selected from the group consisting of $Al_2O_3$, $SiO_2$, and $SiO_2\text{-}Al_2O_3$. The amount of V, Mo, or W in the catalyst layer preferably is limited from 0.1 wt % to 50 wt %. The gas sensitivity and selectivity of gas detecting body 26 is not sufficient when the amount of V, Mo, or W is out of this range.

The catalyst layer, which is made of V and together with either Mo or W supported by a catalyst carrier selected from the group consisting of $Al_2O_3$, $SiO_2$, and $SiO_2\text{-}Al_2O_3$, has excellent gas detecting sensitivity. This is perhaps for the following reason. The V in catalytic layer 28 causes oxidation-reduction. Mo or W creates a solid solution at lattice points of $V^{5+}$ by the isomorphous—replacement, so that the atomic value is controlled and an amount of $V^{4+}$ increases. Thereby, the activity of V is elevated.

In using Mo or W together with V, the supporting amount of V in the catalyst layer preferably is limited from 0.1 wt % to 50 wt % and atomic ratio Mo/V or W/V is preferably limited from 0.05 to 0.5 so as to obtain sufficient detecting sensitivity for practical usage.

The gas detecting element is manufactured, for example, in the following way.

First, a predetermined amount of the support such as $Al_2O_2$, $SiO_2$ and $SiO_2\text{-}Al_2O_3$ is put into a solution, e.g., vanadic solutions that are aqueous solutions of $H_2C_2O_4$-$NH_4VO_3$, $VOSO_4$ etc., molybdic solutions that are aqueous solutions of $(NH_4)_6 Mo_7O_{24}\cdot 4H_2O$, $MoCl_5$, etc., tungstic solutions are aqueous solutions of $(NH_4)W_7O_{24}\cdot 6H_2O$, $WO_2Cl_2$, etc., a mixture of these solutions, and is left in the solution for about 24 hours. The carrier is dried, and the dried carrier is ground in a mortar into powder. This powder is put into a quartz crucible and is calcined at a temperature of 300° C. to 800° C. Thus the catalyst is obtained.

On the other hand, a predetermined amount of binder such as methyl cellulose is added to a ZnO—based oxide semiconductor. Then the binder and semiconductor are mixed in a ball mill to form a paste.

Thereafter, the paste is coated on the insulative body 22 provided with the electrode 24a and 24b and then dried and calcined at 300° C. to 1000° C., thereby forming the gas detecting body 26. This done, the catalyst prepared as mentioned above is dissolved in an appropriate solution to form a paste. This paste is coated on the outer surface of the gas detecting body 26, and then is dried and finally calcined at 300° C. to 1000° C.

Figure 2:
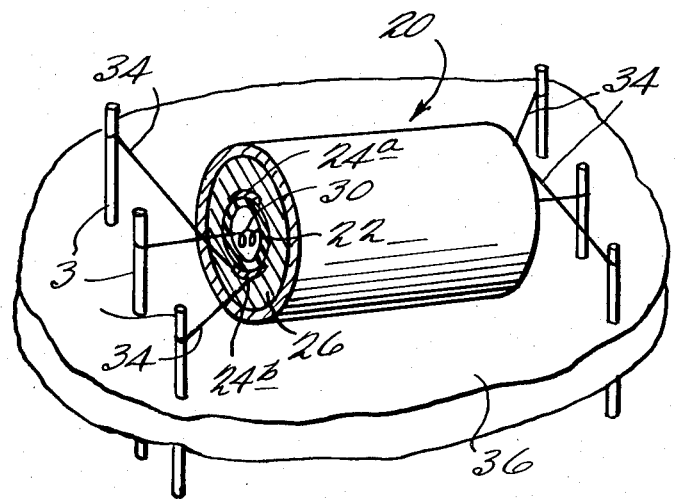
FIG. 2 is a perspective view of a device using the gas detecting element shown in FIG. 1.

The freon gas detecting element 20 manufactured as mentioned above may be fabricated on pins 32 as illustrated in FIG. 2. More specifically, the element 20 is connected by means of lead wire 34 to the pins 32 which are plated on an insulative plate 36.

Examples and controls will be described to prove the effect of the present invention.

EXAMPLES

The catalyst having a chemical composition shown in Examples 1 to 33 of Tables 1 and 2 is coated on the gas detecting body made of a 98 $ZnO\text{-}2Sb_2O_3$.

The gas sensitivity (Ro/Rg) of each example was measured and is as shown in Table 1. In Table 1, "Ro" denotes the electric resistance which each example showed when put in contact with air, "Rg" the electric resistance which each example showed when put in contact with a 500 ppm freon gas.

Control

The catalyst having chemical composition shown in Controls 1 to 6 of Table 3 is coated on the gas detecting body made of a 98 $ZnO\text{-}2Sb_2O_3$. The gas sensitivity (Ro/Rg) of each control was measured and is as shown in Table 3.

TABLE 1

| | | Catalyst Layer | | | Ro/Rg | |
| | | Mo/V | W/V | | | |
| Example | V (wt %) | (atomic ratio) | (atomic ratio) | Carrier | $CHClF_2$ (500 ppm) | $CCl_2F_2$ (500 ppm) |
| --- | --- | --- | --- | --- | --- | --- |
| 1 | 0.1 | — | — | $Al_2O_3$ | 4.0 | 2.8 |
| 2 | " | — | — | $SiO_2$ | 3.6 | 2.5 |
| 3 | " | — | — | $SiO_2$—$Al_2O_3$ | 3.9 | 2.7 |
| 4 | 1.0 | — | — | $Al_2O_3$ | 6.0 | 5.0 |
| 5 | 5.0 | — | — | " | 7.6 | 5.5 |
| 6 | " | — | — | $SiO_2$ | 6.5 | 4.9 |
| 7 | " | — | — | $SiO_2$—$Al_2O_3$ | 7.0 | 5.2 |
| 8 | 10.0 | — | — | $Al_2O_3$ | 8.0 | 6.0 |
| 9 | 50.0 | — | — | " | 5.5 | 3.5 |
| 10 | " | — | — | $SiO_2$ | 3.5 | 3.1 |
| 11 | " | — | — | $SiO_2$—$Al_2O_3$ | 4.0 | 3.4 |
| 12 | 0.1 | 0.1 | — | $Al_2O_3$ | 4.0 | 3.0 |
| 13 | " | — | 0.1 | " | 3.6 | 3.4 |
| 14 | 1.0 | 0.1 | — | " | 6.2 | 5.4 |
| 15 | " | — | 0.1 | " | 6.0 | 5.6 |
| 16 | 5.0 | 0.1 | — | " | 7.8 | 6.0 |
| 17 | " | — | 0.1 | " | 7.2 | 8.0 |
| 18 | 10.0 | 0.1 | — | " | 16.0 | 10.5 |
| 19 | " | — | 0.1 | " | 10.1 | 11.5 |
| 20 | 50.0 | 0.1 | — | " | 6.5 | 5.0 |
| 21 | " | — | 0.1 | " | 5.0 | 5.3 |
| 22 | 1.0 | 0.05 | — | " | 6.1 | 5.1 |
| 23 | " | — | 0.05 | " | 6.1 | 5.3 |
| 24 | " | 0.2 | — | " | 7.0 | 6.0 |
| 25 | " | — | 0.2 | " | 6.8 | 6.2 |

TABLE 1-continued

| Example | V (wt %) | Catalyst Layer Mo/V (atomic ratio) | Catalyst Layer W/V (atomic ratio) | Carrier | Ro/Rg CHClF$_2$ (500 ppm) | Ro/Rg CCl$_2$F$_2$ (500 ppm) |
|---|---|---|---|---|---|---|
| 26 | " | 0.5 | — | " | 6.2 | 5.2 |
| 27 | " | — | 0.5 | " | 6.1 | 5.3 |

TABLE 2

| Example | Catalyst Layer Mo (wt %) | Catalyst Layer W (wt %) | Carrier | Ro/Rg CHClF$_2$ (500 ppm) | Ro/Rg CCl$_2$F$_2$ (500 ppm) |
|---|---|---|---|---|---|
| 28 | 2.0 | — | Al$_2$O$_3$ | 6.5 | 4.0 |
| 29 | 2.0 | — | SiO$_2$ | 4.6 | 2.4 |
| 30 | 2.0 | — | SiO$_2$—Al$_2$O$_3$ | 5.8 | 3.0 |
| 31 | — | 2.0 | Al$_2$O$_3$ | 7.5 | 6.0 |
| 32 | — | 2.0 | SiO$_2$ | 6.0 | 5.0 |
| 33 | — | 2.0 | SiO$_2$—Al$_2$O$_3$ | 7.0 | 5.5 |

TABLE 3

| Control | Pt (wt %) | Pd (wt %) | Rh (wt %) | Carrier | Ro/Rg CHClF$_2$ (2000 ppm) | Ro/Rg CCl$_2$F$_2$ (2000 ppm) |
|---|---|---|---|---|---|---|
| 1 | 2.0 | — | — | Al$_2$O$_3$ | 1.5 | 1.2 |
| 2 | — | 2.0 | — | " | 4.0 | 2.0 |
| 3 | — | — | 2.0 | " | 2.5 | 1.2 |
| 4 | 2.0 | — | — | SiO$_2$ | 1.3 | 1.1 |
| 5 | — | 2.0 | — | " | 3.8 | 1.2 |
| 6 | — | — | 2.0 | " | 2.4 | 1.1 |

An apparent from these results, in the freon gas detecting element according to the present invention the gas sensitivity for the freon gas of 500 ppm is larger than the gas sensitivity for the freon gas of 2000 rpm of the control elements, has good gas sensitivity for the freon gas with low concentration as well as high concentration. Particularly, the element, the catalyst of which is made of V together with either Mo or W supported by one carrier selected from the group consisting of Al$_2$O$_3$, SiO$_2$, and SiO$_2$-Al$_2$O$_3$, has excellent gas sensitivity.

Moreover, the freon gas detecting element according to the present invention is good in gas selectivity, stability of gas detecting sensitivity and reliability. It also is smaller in size than prior art freon gas detectors.

Many changes and modifications in the above-described embodiments can, of course, be carried out without departing from the scope of the present invention. That scope is intended to be limited only by the scope of the appended claims.

What is claimed is:

1. A freon gas detecting element comprising:
a pair of electrodes;
a gas detecting body made of metal oxide semiconductor and covering said pair of electrodes; and
a catalyst layer coated on said gas detecting body, said catalyst layer being made of V and W supported by one catalyst carrier selected from the group consisting of Al$_2$O$_3$, SiO$_2$, and SiO$_2$-Al$_2$O$_3$, the amount of V in said catalyst layer being limited from about 0.1 wt % to about 50 wt %, and the atomic ratio (W/V) between said V and W being limited from about 0.05 to about 0.5.

2. A freon gas detecting element comprising:
a pair of electrodes;
a gas detecting body made of metal oxide semiconductor spread on said pair of electrodes; and
a catalyst layer coated on said gas detecting body, said layer being made of V and Mo supported by one catalyst carrier selected from the group consisting of Al$_2$O$_3$, SiO$_2$, and SiO$_2$-Al$_2$O$_3$, the amount of said V in said catalyst layer being limited from about 0.1 wt % to about 50 wt % and the atomic ratio (Mo/V) between said V and Mo being limited from about 0.05 to about 0.5.

3. A freon gas detecting element according to claim 1 or 2, wherein said detecting body is made of a ZnO-based semiconductor.

4. A freon gas detecting element according to claim 1 or 2, wherein said gas detecting body is made of a metal oxide semiconductor selected from the group consisting of ZnO, SnO$_2$, Fe$_2$O$_3$, ZnO-Me$_2$O$_3$ (Me=Sb or Cr), SnO$_2$-Me$_2$O$_3$ (Me=Sb or Cr), and Fe$_2$O$_3$-Me$_2$O$_3$ (Me=Sb or Cr).

5. A freon gas detecting element according to claim 1 or 2, wherein said pair of electrodes is disposed on the outer periphery of a hollow cylindrical insulative body.

6. A freon gas detecting element according to claim 5, further including a heater detachably disposed in the hollow interior of said insulative body for heating said gas detecting body.

* * * * *